(12) United States Patent
Briem et al.

(10) Patent No.: US 6,514,969 B2
(45) Date of Patent: Feb. 4, 2003

(54) β-AMYLOID INHIBITORS, PROCESSES FOR PREPARING THEM, AND THEIR USE IN PHARMACEUTICAL COMPOSITIONS

(75) Inventors: Hans Briem, Bremen (DE); Klaus Mendla, Ingelheim (DE); Helmut Michael Romig, Gau-Algesheim (DE); Katja Fechteler, Wiesbaden (DE); Klaus Fuchs, Gau-Algesheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/911,825

(22) Filed: Jul. 24, 2001

(65) Prior Publication Data

US 2002/0042420 A1 Apr. 11, 2002

Related U.S. Application Data

(60) Provisional application No. 60/227,039, filed on Aug. 23, 2000.

(30) Foreign Application Priority Data

Aug. 16, 2000 (DE) .......................................... 100 40 016

(51) Int. Cl.$^7$ .................... C07D 401/14; C07D 403/00; C07D 413/00; A61K 31/445; A61P 25/00
(52) U.S. Cl. .................... 514/233.2; 546/199; 544/129; 544/364; 514/322; 514/253.09
(58) Field of Search .................... 546/199; 514/322, 514/253.09, 233.2; 544/129, 364

(56) References Cited

U.S. PATENT DOCUMENTS

| | | | |
|---|---|---|---|
| 4,382,938 A | * | 5/1983 | Kaplan et al. .............. 424/256 |
| 6,030,984 A | | 2/2000 | Trottmann et al. .......... 514/306 |

FOREIGN PATENT DOCUMENTS

EP 0092458 A2 10/1983

OTHER PUBLICATIONS

CAS printout for Lombardino et al.*
Sinha et al. Cellular mechanisms of beta–amyloid production and secretion, Proc. Natl. Acad. Sci., 96:11049–11053.*
Lombardino, Joseph G., "Preparation and New Reactions of Imidazo[1,2–a]pyridines", Journal of Organic Chemistry, Jul. 1965, No. 7, vol. 12, 2403–2407, XP001055720.
Loeber, Stefan et al, "Azaindole Derivatives with High Affinity for the Dopamine D4 Receptor: Synthesis, Ligand Binding Studies and Comparison of Molecular Electrostatic Potential Maps", Bioorganic & Medicinal Chemistry Letters 9, 1999, 97–102.
Gupta, S.P. et al, "Quantative Structure–Activity Relationship Studies on Some Nonbenzodiazepine Series of Compounds Acting at the Benzodiazepine Receptor", Bioorganic & Medicinal Chemistry 6, 1998, 2213–2218, XP–000872293.
Trapani, Giuseppe et al, "Synthesis and Binding Affinity of 2–Phenylimidazo[1,2–a]pyridine Derivatives for both Central and Peripheral Benzodiazepine Receptors. A New Series of High–Affinity and Selective Ligands for the Peripheral Type", J. Med. Chem., 1997, vol. 40, 3109–3118, XP002900938.

* cited by examiner

*Primary Examiner*—Richard L. Raymond
*Assistant Examiner*—Hong Liu
(74) *Attorney, Agent, or Firm*—Robert P. Raymond; Timothy X. Witkowski; Mary-Ellen Devlin

(57) ABSTRACT

Compounds of general formula (I)

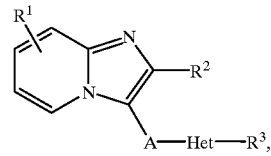

(I)

wherein:

A is —CH$_2$—, —CH$_2$—CH$_2$—, —CH$_2$—CH$_2$—CH$_2$—, —CH$_2$—CH$_2$—CH$_2$—CH$_2$—, —CH$_2$—CO—, —CH$_2$—CH$_2$—CO—, or —CH=CH—CO—;

Het is piperidinyl, piperazinyl, or dihydrobenzimidazolonyl;

R$^1$ is hydrogen or halogen;

R$^2$ is hydrogen, C$_1$–C$_4$-alkyl, CF$_3$, or a phenyl group optionally substituted by halogen, C$_1$–C$_4$-alkyl, or C$_1$–C$_4$-alkyloxy; and R$^3$ is hydrogen, C$_1$–C$_4$-alkyl, HO—C$_1$–C$_4$-alkyl, or C$_2$–C$_4$-alkenyl; or a group selected from phenyl, benzyl, and phenylethyl, each optionally substituted by halogen, CF$_3$, C$_1$–C$_4$-alkyl, or C$_1$–C$_4$-alkyloxy; or a heterocycle selected from among morpholine, piperidine, piperazine, and dihydrobenzimidazolone, the heterocycle either linked directly or via a C$_1$–C$_4$-alkylene bridge, or an optical isomer, enantiomer, tautomer, free base, or pharmacologically acceptable acid addition salt thereof; methods of making such compounds; pharmaceutical compositions thereof, and their use in treating or preventing diseases in which a therapeutic benefit can be obtained by interfering in the process of the formation of Aβ or its release from cells, by inhibiting the Aβ activity, such as Alzheimer's disease, Parkinson's disease, and Huntington's Chorea.

16 Claims, No Drawings

β-AMYLOID INHIBITORS, PROCESSES FOR PREPARING THEM, AND THEIR USE IN PHARMACEUTICAL COMPOSITIONS

The present invention relates to compounds of general formula (I)

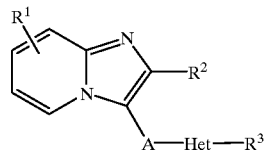

(I)

wherein the groups A, Het, $R^1$, $R^2$, and $R^3$ may have the meanings given in the following description and in the claims, processes for preparing them and the use of compounds of general formula (I) as pharmaceutical compositions, particularly as pharmaceutical compositions with a beta-amyloid-inhibiting activity.

BACKGROUND OF THE INVENTION

The aggregation and precipitation of proteins are implicated in the origins of various neurodegenerative disorders such as Alzheimer's, Parkinson's, and St. Vitus' dance ("Huntington's Chorea"). In Alzheimer's disease, the amyloid-β-peptide (Aβ) aggregates and leads to insoluble senile plaques which constitute one of the pathological markers of the disease. Aβ is formed by the proteolytic cleaving of a precursor protein, amyloid precursor protein (APP). Two methods of metabolizing APP have been detected, the non-amyloidogenic method and the amyloidogenic method.

In the non-amyloidogenic metabolism of APP, α-secretase cleaves within the Aβ region of the APP and thus leads to the secretion of the soluble N-terminal region of the protein (α-APPs) and, after the γ-secretase cutting has taken place, to the release of p3. By contrast, the amyloidogenic route leads to the formation of AP, two proteases generating the N-terminus (β-secretase), and the C-terminus (γ-secretase), respectively, of Aβ.

Aβ can be detected in human plasma and cerebrospinal fluid in vivo. In cell culture, too, secreted Aβ can be detected in the cell culture supernatant of various types of cells which express or overexpress APP or fragments thereof endogenously.

The problem of the present invention is to prepare compounds which are capable of interfering (preferably in an inhibitory capacity) in the process of the formation of Aβ or its release from cells, or of reducing the activity of Aβ by inhibiting it. Finally, the present invention is based on the further objective of preparing compounds which can be used effectively for the prevention or treatment of Alzheimer's disease.

DETAILED DESCRIPTION OF THE INVENTION

The problems set forth above are solved by the compounds of general formula (I) defined as follows.

The compounds according to the invention are compounds of general formula (I)

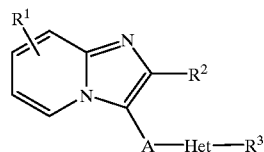

(I)

wherein
A denotes —$CH_2$—, —$CH_2$—$CH_2$—, —$CH_2$—$CH_2$—$CH_2$—, —$CH_2$—$CH_2$—$CH_2$—$CH_2$—, —$CH_2$—CO—, —$CH_2$—$CH_2$—CO—, or —CH=CH—CO—;
Het denotes piperidinyl, piperazinyl, or dihydrobenzimidazolonyl;
$R^1$ denotes hydrogen or halogen, preferably hydrogen;
$R^2$ denotes hydrogen, $C_1$–$C_4$-alkyl, $CF_3$, or a phenyl group which may optionally be substituted by halogen, $C_1$–$C_4$-alkyl, or $C_1$–$C_4$-alkyloxy; and
$R^3$ denotes hydrogen, $C_1$–$C_4$-alkyl, HO—$C_1$–$C_4$-alkyl, $C_2$–$C_4$-alkenyl, or a group selected from among phenyl, benzyl, and phenylethyl, which may optionally be substituted by halogen, $CF_3$, $C_1$–$C_4$-alkyl, or $C_1$–$C_4$-alkyloxy, or a heterocycle selected from among morpholine, piperidine, piperazine, and dihydrobenzimidazolone, which may be linked directly or via a $C_1$–$C_4$-alkylene bridge.

Preferred compounds of general formula (I) are those wherein:
A denotes —$CH_2$—$CH_2$—, —$CH_2$—$CH_2$—$CH_2$—, —$CH_2$—CO—, or —CH=CH—CO—;
Het denotes piperidinyl, piperazinyl, or dihydrobenzimidazolonyl;
$R^1$ denotes hydrogen or halogen, preferably hydrogen;
$R^2$ denotes hydrogen, $C_1$–$C_4$-alkyl, phenyl, halogen-substituted phenyl, $C_1$–$C_4$-alkyloxy-substituted phenyl, or $CF_3$; and
$R^3$ denotes $C_1$–$C_4$-alkyl, HO—$C_1$–$C_4$-alkyl, $C_2$–$C_4$-alkenyl, phenyl, benzyl, phenylethyl, halogen-substituted phenyl, halogen-substituted benzyl, or a heterocycle selected from among morpholine and dihydrobenzimidazolone, which may be linked directly or via a $C_1$–$C_4$-alkylene bridge.

Particularly preferred compounds of general formula (I) are those wherein:
A denotes —$CH_2$—$CH_2$—, —$CH_2$—$CH_2$—$CH_2$—, —$CH_2$—CO—, or —CH=CH—CO—;
Het denotes piperidinyl, piperazinyl, or dihydrobenzimidazolonyl;
$R^1$ denotes hydrogen or chlorine, preferably hydrogen;
$R^2$ denotes hydrogen, methyl, phenyl, or 4-chlorophenyl; and
$R^3$ denotes $C_1$–$C_4$-alkyl, HO—$C_1$–$C_4$-alkyl, $C_2$–$C_4$-alkenyl, phenyl, benzyl, halogen-substituted benzyl, or a heterocycle selected from morpholine and dihydrobenzimidazolone, which may be linked directly or via a $C_1$–$C_4$-alkylene bridge.

Of particular importance according to the invention are compounds of general formula (I), wherein:
A denotes —$CH_2$—$CH_2$—, —$CH_2$—$CH_2$—$CH_2$—, or —CH=CH—CO—;
Het denotes piperidinyl or piperazinyl;
$R^1$ denotes hydrogen or chlorine, preferably hydrogen;
$R^2$ denotes hydrogen, methyl, phenyl, or 4-chlorophenyl; and
$R^3$ denotes 2-hydroxyethyl, phenyl, benzyl, 4-chlorobenzyl, or 1,3-dihydrobenzimidazol-2-on-1-yl.

Also preferred are compounds of general formula (I) wherein:

A denotes —CH$_2$—CH$_2$—, —CH$_2$—CH$_2$—CH$_2$—, or —CH=CH—CO—;
Het denotes piperidinyl or piperazinyl;
R$^1$ denotes hydrogen;
R$^2$ denotes hydrogen, methyl, phenyl, or 4-chlorophenyl; and
R$^3$ denotes benzyl, 4-chlorobenzyl, or 1,3-dihydrobenzimidazol-2-on-1-yl.

Of exceptional importance according to the invention are the compounds of general formula (I), wherein the group —Het—R$^3$ denotes

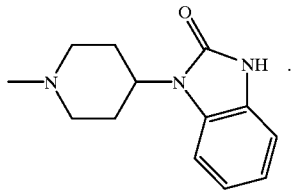

The compounds listed below are mentioned as being particularly important within the scope of the present invention:
(a) 1-{1-[2-(2-methylimidazo[1,2-a]pyridin-3-yl)ethyl]piperidin-4-yl}-1,3-dihydrobenzimidazol-2-one;
(b) 1-[1-(3-imidazo[1,2-a]pyridin-3-ylpropyl)piperidin-4-yl]-1,3-dihydrobenzimidazol-2-one;
(c) 1-[1-(2-imidazo[1,2-a]pyridin-3-ylethyl)piperidin-4-yl]-1,3-dihydrobenzimidazol-2-one; and
(d) 1-{1-[3-(2-phenylimidazo[1,2-a]pyridin-3-yl)propyl]piperidin-4-yl}-1,3-dihydrobenzimidazol-2-one.

The invention relates to the compounds in question, optionally in the form of the individual optical isomers, mixtures of the individual enantiomers or racemates, in the form of the tautomers and in the form of the free bases or the corresponding acid addition salts with pharmacologically acceptable acids, such as, for example, acid addition salts with hydrohalic acids, e.g., hydrochloric or hydrobromic acid, or organic acids, such as oxalic, fumaric, diglycolic, or methanesulfonic acid.

The term alkyl groups (including those which are part of other groups) denotes branched and unbranched alkyl groups with 1 to 4 carbon atoms, unless otherwise specified. Examples include: methyl, ethyl, propyl, and butyl. Unless otherwise stated, the above terms propyl and butyl also include all the possible isomeric forms. For example, the term propyl also includes the two isomeric groups n-propyl and isopropyl and the term butyl includes n-butyl, isobutyl, sec-butyl, and tert-butyl. In some cases common abbreviations are also used to denote the abovementioned alkyl groups, such as Me for methyl, Et for ethyl, etc.

The term alkylene groups denotes branched and unbranched alkylene bridges with 1 to 4 carbon atoms. Examples include: methylene, ethylene, propylene, and butylene. Unless otherwise stated, the terms propylene and butylene used above also include all the possible isomeric forms. Accordingly, the term propylene also includes the two isomeric bridges n-propylene and dimethylmethylene and the term butylene includes the isomeric bridges n-butylene, 1-methylpropylene, 2-methylpropylene, 1,1-dimethylethylene, and 1,2-dimethylethylene.

The term alkenyl groups (including those which are part of other groups) denotes branched and unbranched alkenyl groups with 2 to 4 carbon atoms, provided that they have at least one double bond, such as, for example, vinyl (provided that no unstable enamines or enolethers are formed), propenyl, isopropenyl, and butenyl.

The term halogen generally denotes fluorine, chlorine, bromine, or iodine. Unless otherwise specified, chlorine is preferred within the scope of the present invention.

"=O" denotes an oxygen atom linked via a double bond.

In the definitions given above, all the definitions given for the groups A and Het according to general formula (I) should be regarded as double-bonded groups. The groups A, unless they are the asymmetric bridge members —CH$_2$—CO—, —CH$_2$—CH$_2$—CO—, or —CH=CH—CO—, should be linked to their neighboring groups in two different orientations. The preferred orientation according to the invention is the one in which the carbonyl function of the bridge members mentioned above is bonded directly to the group "Het". The group Het may also be linked to its neighboring groups in various orientations. The preferred orientation according to the invention is the one in which the group Het is linked by at least one nitrogen atom to the bridge A. Most preferably, the groups piperazinyl and dihydrobenzimidazolonyl defined as Het groups are also linked to the group R$^3$ via their second N atom.

By dihydrobenzimidazolonyl is meant 1,3-dihydrobenzimidazol-2-on-1-yl.

According to another aspect, the present invention relates to the use of the compounds of general formula (I) defined above as pharmaceutical compositions. In particular, the present invention relates to the use of the compounds of general formula (I) for preparing a pharmaceutical composition for the prevention and/or treatment of diseases in which a therapeutic benefit can be achieved by interfering (preferably in an inhibitory capacity) in the process of the formation of Aβ or its release from cells. It is preferred according to the invention to use compounds of general formula (I) as specified above in order to prepare a pharmaceutical composition for the prevention and/or treatment of Alzheimer's disease.

One approach to synthesizing the compounds of general formula (I) according to the invention may involve the use of various methods, optionally based on or using conventional chemical methods of synthesis as described in more detail hereinafter.

One possible method of synthesizing the compounds of general formula (I) wherein A denotes an ethylene bridge is shown in Diagram 1.

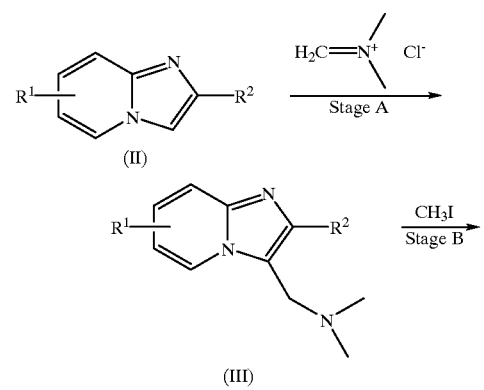

Diagram 1

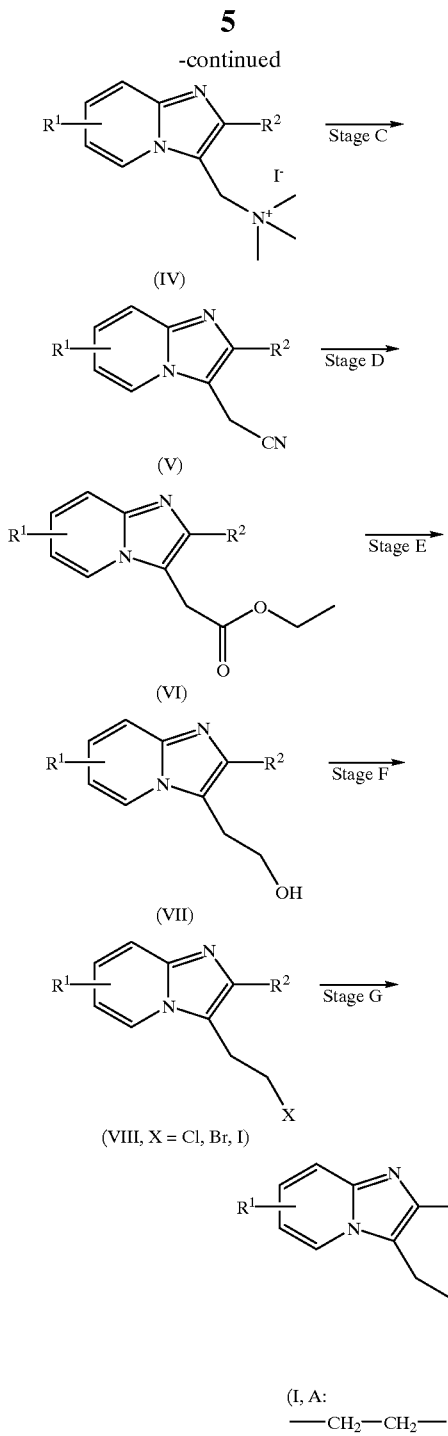

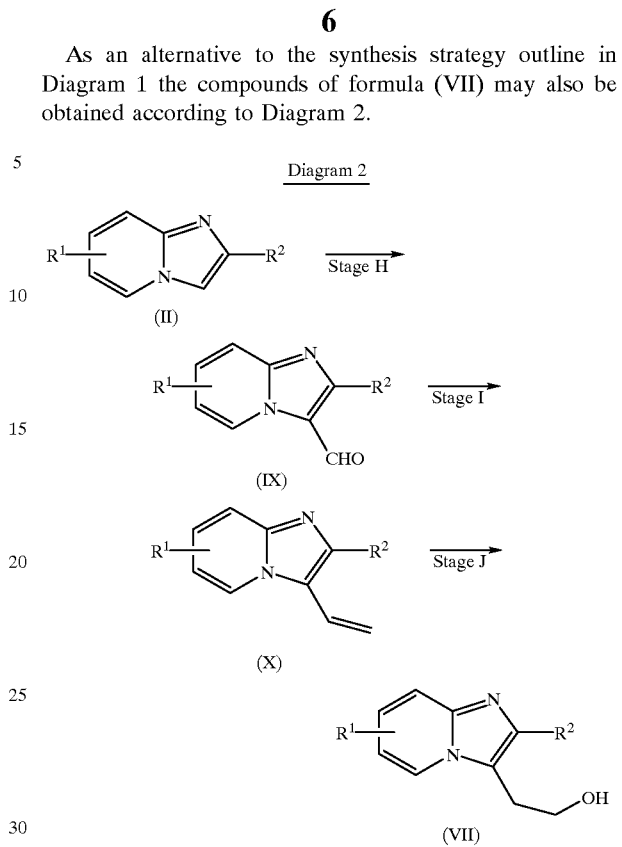

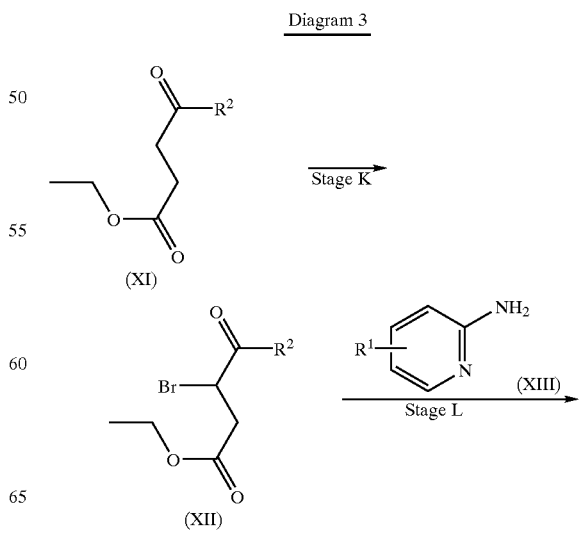

Diagram 1:

In a first step (stage A) a 2H-imidazo[1,2-a]pyridine (II) is converted, by reaction with N,N-dimethylmethyleneiminium chloride, into the aminomethyl-substituted compounds (III) from which the quaternary ammonium salts (IV) can be obtained by alkylation with methyl iodide (stage B). These can then be converted into the nitriles (V) (stage C), which when hydrolyzed yield the carboxylic acid esters (VI) (stage D). Reduction of the compounds (VI) according to stage E leads to the alcohols (VII) which are converted in stage F into the halides (VIII). The compounds of formula (I) wherein A denotes —$CH_2$—$CH_2$— may be obtained therefrom by nucleophilic substitution (stage G).

As an alternative to the synthesis strategy outline in Diagram 1 the compounds of formula (VII) may also be obtained according to Diagram 2.

Diagram 2:

For this, the 2H-imidazo[1,2-a]pyridines (II) are converted in a Vilsmeier reaction into the formylated 2H-imidazo[1,2-a]pyridines (IX) (stage H). From these, the olefins (X) can be obtained by Wittig reaction (stage I). The alcohols (VII) may be obtained according to stage J by hydroboration of the compounds (X).

Another variant of the process enables the compounds of formula (VI) to be obtained in a different manner from Diagram 1. This is shown in Diagram 3.

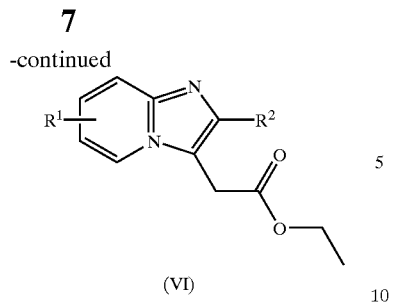

(VI)

Diagram 3:

Starting from the carbonyl compounds (XI), the α-bromocarbonyl compounds (XII) may be obtained by bromination (stage K). After reaction with 1-aminopyridines of formula (XIII) these compounds (XII) lead to the esters (VI) (stage L).

Compounds of formula (I) wherein A denotes the bridge —$CH_2$—CO— may be obtained from the esters of formula (VI) by an alternative method to that shown in Diagram 1. They may then in turn be converted into compounds of formula (I) wherein A denotes —$CH_2$—$CH_2$— (Diagram 4).

Diagram 4

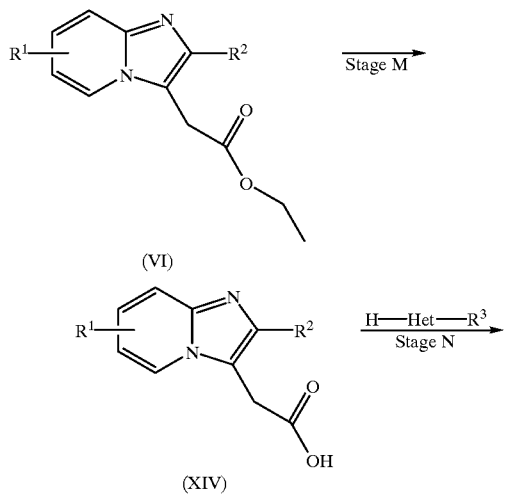

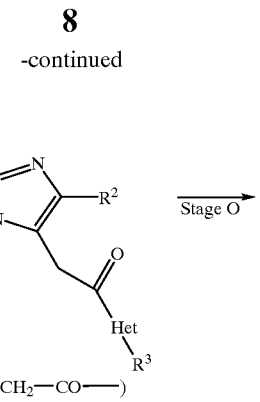

(I with A—$CH_2$—CO—)

(I with A—$CH_2$—$CH_2$—)

Diagram 4:

The saponification of the esters (VI) leads, according to stage M, to the free carboxylic acids (XIV). These may optionally be converted according to stage N by reacting with the amines H—Het—$R^3$, using suitable coupling reagents, into the corresponding amides (I, where A is —$CH_2$—CO), which can be reductively transformed into the corresponding compounds of formula (I) wherein A equals —$CH_2$—$CH_2$— (stage O).

For preparing compounds of formula (I) wherein A denotes —$CH_2$—$CH_2$—$CH_2$— or —CH=CH—CO—, the procedure illustrated in Diagram 5 may be used.

Diagram 5

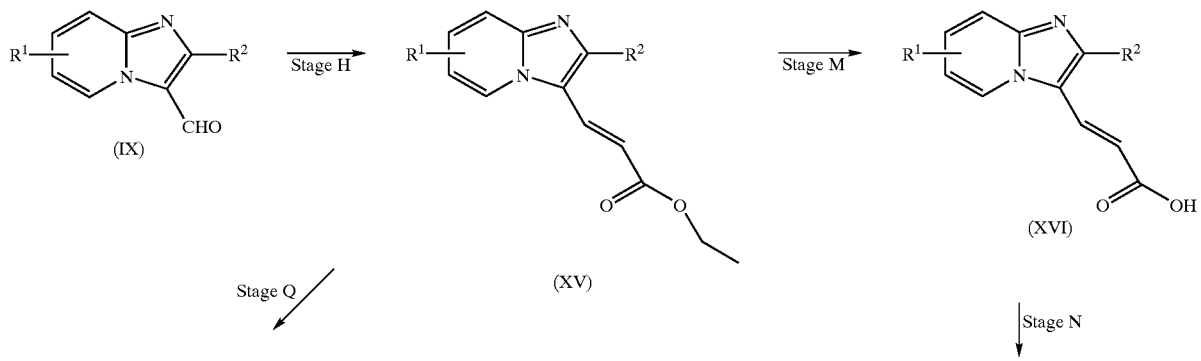

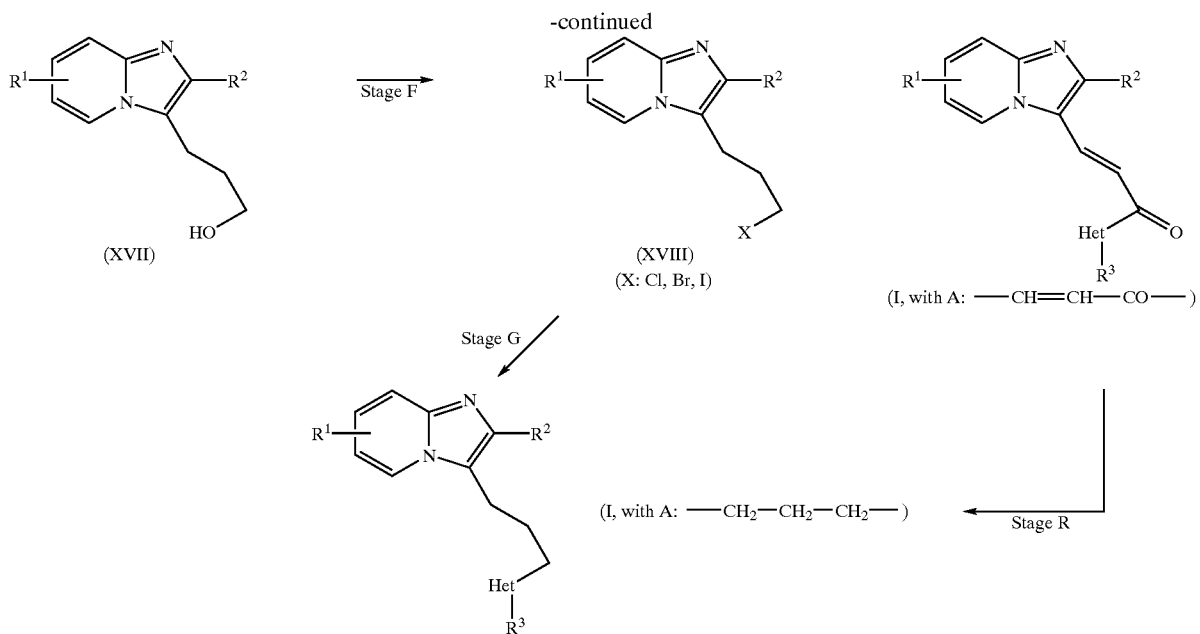

Diagram 5:

Starting from the carbonylated compounds (IX) the α,β-unsaturated esters (XV) are synthesized by a Wittig or Wittig-Homer-Emmons reaction (stage H). If the esters (XV) according to stage M are saponified to form the carboxylic acids (XVI), these may be converted according to stage N into the α,β-unsaturated amides (I, where A is —CH=CH—CO—). From these, the compounds of formula (I) wherein A denotes propylene can be obtained reductively (stage R). Alternatively, the latter may be obtained by reduction (stage Q) of the esters (XV) to form the alcohols (XVII), which give access to the target compounds by standard methods (stages F and G) via the halides (XVIII).

Another alternative process (cf. Diagram 6) provides a method of obtaining the compounds of formula (XVII) different from that shown in Diagram 5 and on the other hand yields the compounds of formula (I) wherein A denotes —CH$_2$—CH$_2$—CO—.

Diagram 6

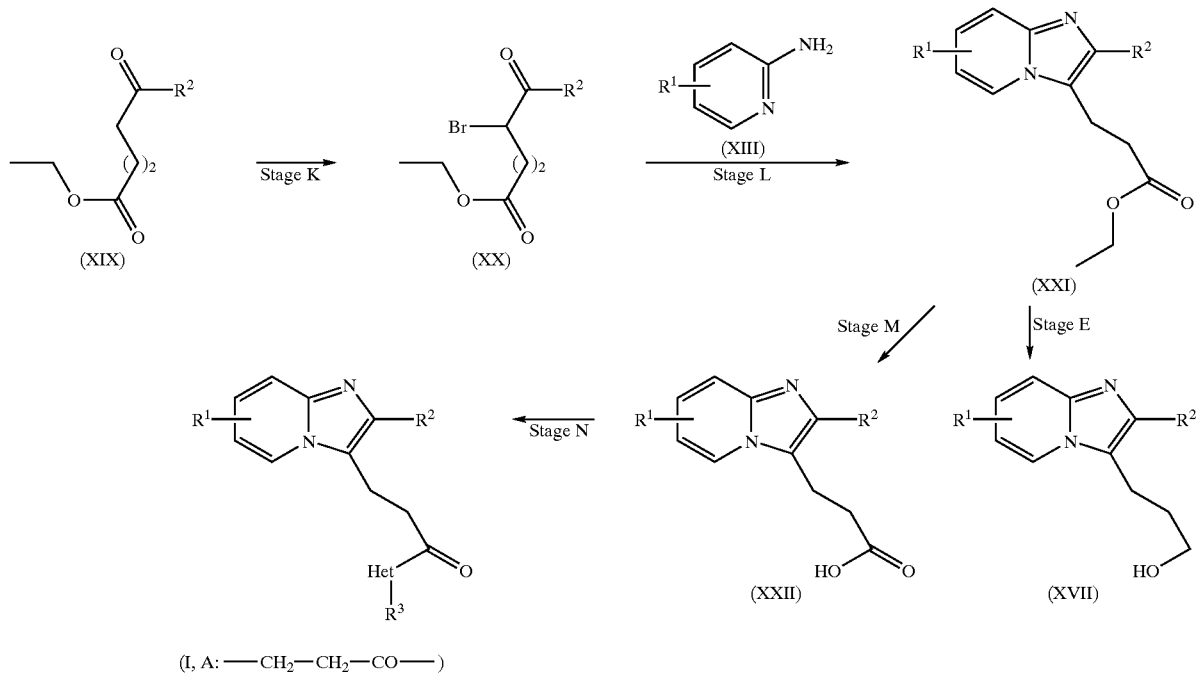

Diagram 6:

Starting from the carbonyl compounds (XIX) bromination produces the α-bromocarbonyl compounds (XX) (stage K), which when reacted with 1-aminopyridines of formula (XIII) provides access to the esters (XXI) (stage L). These may be converted, on the one hand, according to stage E, into the alcohols (XVII), while on the other hand, after saponification (stage M) to yield the carboxylic acids (XXII), they may also be used as starting compounds for preparing the compounds of formula (I) wherein A denotes —CH$_2$—CH$_2$—CO—. The latter may be converted reductively, analogously to stage O (cf. Diagram 4), into the compounds of general formula (I) wherein A denotes —CH$_2$—CH$_2$—CH$_2$—.

In the methods of synthesis described above it may be appropriate to use common protecting groups which may be both introduced and cleaved by standard methods.

The examples of synthesis which follow are intended only as an illustration without restricting the object of the invention.

EXAMPLE 1

1-[1-(2-imidazo[1,2-a]pyridin-3-yl-ethyl)piperidin-4-yl]-1,3-dihydrobenzimidazol-2-one

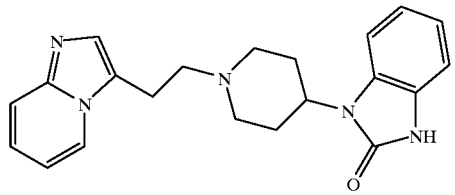

1.1.: 3-N,N-dimethylaminomethylimidazo[1,2-a]pyridine (Corresponds to the Compound of Formula (III)
Process According to Stage A:

13.0 g (110 mmol) of 2H-imidazo[1,2-a]pyridine in 120 ml acetonitrile is combined with 21.0 g (224 mmol) of N,N-dimethylmethyleneiminium chloride and stirred for 6 hours at 65° C. After 16 hours standing at ambient temperature, the mixture is concentrated to 70 ml. The crystals precipitated are suction filtered, dissolved in 60 ml of water, and made alkaline with concentrated sodium hydroxide solution. The mixture is extracted with ethyl acetate, the organic phases are dried and concentrated by evaporation. 19.2 g of the product is obtained as white crystals.

1.2.: 3-N,N,N-Trimethylammoniummethylimidazo[1,2-a]pyridine Iodide (Corresponds to the Compound of Formula (IV)
Process According to Stage B:

19.2 g (110 mmol) of the compound of Example 1.1. is dissolved in 120 ml ethanol and combined with 21.0 g (147 mmol) of methyl iodide. The mixture is stirred for 4 hours at ambient temperature. It is then combined with 50 ml ether and cooled with an ice bath. After the crystals have been suction filtered and dried, 31.0 g of product is obtained.

1.3.: 3-Cyanomethylimidazo[1,2-a]pyridine (Corresponds to the Compound of Formula (V)
Process According to Stage C:

31.0 g (97.8 mmol) of the compound of Example 1.2. in 220 ml ethanol is combined with 16.0 g (326 mmol) of sodium cyanide and refluxed for 16 hours. The mixture is evaporated down, combined with 100 ml of water, and extracted with ethyl acetate. The organic phases are evaporated down and the residue is recrystallized from toluene. After washing with ether, 6.40 g of product is obtained.

1.4.: 3-ethoxycarbonylmethylimidazo[1,2-a]pyridine (Corresponds to the Compound of Formula (VI)
Process According to Stage D:

15 ml of concentrated sulfuric acid is added to 38 ml of ethanol. 6.40 g (40.8 mmol) of the compound of Example 1.3 is added and the mixture is refluxed for 6 hours; then the mixture is left to stand for 16 hours. The mixture is then added to 30 ml of ice/water and carefully adjusted to pH 10 with potassium carbonate. It is extracted with ethyl acetate, the combined organic phases are dried and evaporated down. The residue is decocted three times with ether and 5.50 g of the product is precipitated by careful evaporation.

1.5.: 3-(2-hydroxyethyl)imidazo[1,2-a]pyridine (Corresponds to the Compound of Formula (VII))
Process According to Stage E:

A solution of 3.30 g (29.7 mmol) of anhydrous calcium chloride in 35 ml of ethanol is combined with a solution of 5.50 g (27.0 mmol) of the compound of Example 1.4, dissolved in 50 ml of THF. This is cooled to –10° C. and 2.26 g (59.7 mmol) of sodium borohydride is added in batches. The resulting mixture is heated to ambient temperature, stirred for 6 hours and then left to stand for 16 hours at 4° C. The mixture is combined with 2 N HCl and then made alkaline with concentrated ammonia solution. The organic solvent is distilled off and the aqueous phase is adjusted to pH 11 with potassium carbonate. Extraction with ethyl acetate, evaporation, and drying at 40° C. yields 3.80 g of yellow crystals.

Alternative processes for preparing the compounds of general formula (VII) according to stages H, I, and J:

1.5.1.: 3-Formylimidazo[1,2-a]pyridine (Corresponds to the Compound of Formula (IX))
Process According to Stage H:

64.9 g (423 mmol) of phosphorus oxychloride is added dropwise to 70.4 g (846 mmol) of DMF within 50 minutes, while cooling with ice, in such a way that the temperature remains at 2° C.–5° C. The mixture is stirred for 1 hour at 5° C. and then 25.0 g (212 mmol) of 2H-imidazo[1,2-a]pyridine in 30 ml of DMF is added dropwise at 5° C.–10° C. It is then stirred for 1 hour at 5° C. and then heated for 6 hours to 100° C. 100 ml of water is then added dropwise while cooling with ice and the pH is adjusted to 7 with 40 ml of concentrated ammonia solution. The mixture is extracted exhaustively with dichloromethane, the organic phase is washed with water, dried, and evaporated down. After purification of the crude product by flash chromatography (dichloromethane/ethanol 95:5), 11.3 g of product is obtained.

1.5.2.: 3-Vinylimidazo[1,2-a]pyridine (Corresponds to the Compound of Formula (X))
Process According to Stage I:

1.00 g (6.89 mmol) of the compound of Example 1.5.1 dissolved in 30 ml of THF is taken and 3.70 g (10.4 mmol) of methyltriphenylphosphonium bromide is added. After 10 minutes, 3.01 g of potassium tert-butoxide dissolved in 35 ml of THF is added dropwise, during which time the reaction mixture heats up somewhat. The reaction mixture is stirred for 4 hours at ambient temperature, combined with 10 ml of water, and the clear solution is stirred for 10 minutes. The organic phase is separated off and the aqueous phase is extracted with dichloromethane. This is dried, evaporated down, and the residue is purified by flash chromatography (dichloromethane/ethanol 95:5). In this way, 480 mg of crystalline product was obtained.

1.5.: 3-(2-hydroxyethyl)imidazo[1,2-a]pyridine (Corresponds to the Compound of Formula (VII))
Process According to Stage J:

735 mg (8.74 mmol) of 2,3-dimethyl-2-butene is added dropwise, under protective gas, to 4.37 ml (8.74 mmol) of a 2 M solution of borane dimethylsulfide complex in THF. Then the mixture is stirred for 2.5 hours at 5° C. to 10° C. and this solution is added dropwise to 420 mg (2.91 mmol) of the compound of Example 1.5.2 dissolved in 15 ml of THF and 15 ml of dichloromethane. The mixture is left to react for 16 hours and, while it is cooled, 4.7 ml of ethanol, then 13 ml of 2 sodium hydroxide solution and then 6.3 ml of hydrogen peroxide solution (30%) is added. It is then stirred for 3 hours at ambient temperature. The organic phase is separated off and the aqueous phase is extracted with dichloromethane. The combined organic phases are dried and evaporated down. They are purified by flash chromatography (gradient: dichloromethane/ethanol 90:10 to 70:30) and in this way 136 mg of product is obtained.

1.6.: 3-(2-Bromoethyl)imidazo[1,2-a]pyridine (Corresponds to the Compound of Formula (VIII))

Process According to Stage F:

2.31 g (14.3 mmol) of the compound of Example 1.5 is dissolved in 20 ml of chloroform. 4.00 g (19.2 mmol) of thionyl bromide is added dropwise, within 10 minutes, while cooling with ice. After the mixture has been stirred initially for 4 hours, while cooling with ice, it is stirred for a further 16 hours at ambient temperature. 20 ml of THF is added and the precipitation is completed after 10 minutes by the addition of 20 ml of ether. After 30 minutes stirring in the ice bath, it is centrifuged. Precipitation of the crystals yields 2.35 g of crude product in the form of the hydrobromide.

1.7.: 1-[1-(2-imidazo[1,2-a]pyridin-3-ylethyl)piperidin-4-yl]-1,3-dihydrobenzimidazol-2-one Process According to Stage G:

2.35 g (6.4 mmol) of the hydrobromide of Example 1.6 is dissolved in 30 ml of DMF and 70 ml of acetone, then 1.43 g (6.58 mmol) of 1-piperidin-4-yl-1,3-dihydrobenzimidazol-2-one, 2.80 g (20.3 mmol) of potassium carbonate, and 500 mg (3.01 mmol) of potassium iodide are added and the resulting mixture is heated to 55° C. for 7 hours. It is then stirred for 16 hours at ambient temperature. The solvent is removed and the residue is purified by flash chromatography (dichloromethane/ethanol 90:10). Then it is recrystallized from dichloromethane/ethanol 90:10. 750 mg of free base is dissolved in 10 ml of ethanol and combined with 3 ml of ethereal hydrochloric acid. By recrystallization from methanol and drying at 65° C. in vacuo, 520 mg of product is obtained in the form of the hydrochloride. MS: m/z 362 [(M+H)$^+$]; melting point: 197° C.

EXAMPLE 2

1-[1-[2-(2-methylimidazo[1,2-a]pyridin-3-yl)ethyl]piperidin-4-yl]-1,3-dihydrobenzimidazol-2-one

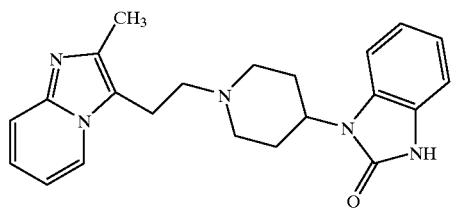

Prepared analogously to Example 1; melting point: 194° C.

EXAMPLE 3

3-{2-[4-(2-hydroxyethyl)piperidine-1-yl]ethyl}-2-methylimidazo[1,2-a]pyridine

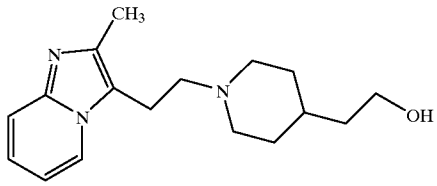

Prepared analogously to Example 1; melting point: oil; MS: m/z 288 [(M+H)$^+$].

EXAMPLE 4

1-[2-(2-methylimidazo[1,2-a]pyridin-3-yl)ethyl]-3-(propen-2-yl)-1,3-dihydrobenzimidazol-2-one

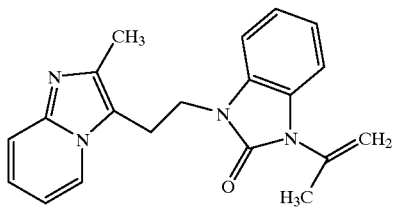

Prepared analogously to Example 1; melting point: 112° C.

EXAMPLE 5

1-[2-(2-methylimidazo[1,2-a]pyridin-3-yl)ethyl]-1,3-dihydrobenzimidazol-2-one

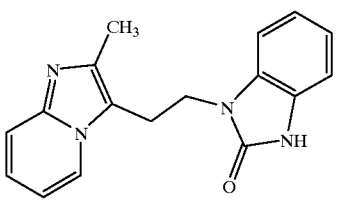

70 mg (0.21 mmol) of Example 4 is dissolved in 2 ml of ethanol and combined with 100 µl of ethanolic hydrochloric acid. The mixture is stirred for 3 hours at ambient temperature, the solvent is eliminated, and 62.4 mg of the product is obtained by crystallization from dichloromethane/ethanol. Melting point: 236° C.

EXAMPLE 6

3-{2-[4-(2-N-Morpholinoethyl)piperazin-1-yl]-2-oxoethyl}-2-phenylimidazo[1,2-a]pyridine

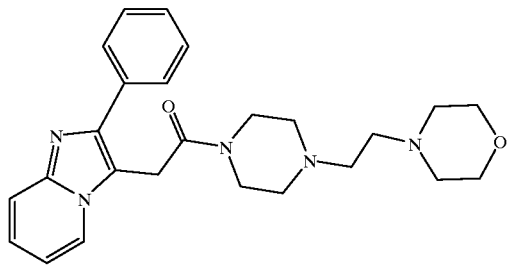

6.1.: 3-Carboxymethyl-2-phenylimidazo[1,2-a]pyridine (Corresponds to the Compound of Formula (XIV))
Process According to Stage M:

3.50 g (12.5 mmol) of 3-ethoxycarbonylmethyl-2-phenylimidazo[1,2-a]pyridine (compound according to formula (VI) obtainable according to stage D) is heated to 100° C. in 200 ml of 2 N hydrochloric acid for 5 hours. The hydrochloric acid is distilled off, the residue is taken up in water and crystallized by the addition of concentrated ammonia solution. In this way, 2.60 g of product is obtained. Melting point: decomp. 243° C.–244° C.

6.2.: 3-{2-[4-(2-N-Morpholinoethyl)piperazin-1-yl]-2-oxoethyl}-2-phenylimidazo[1,2-a]pyridine
Process According to Stage N:

230 mg (0.99 mmol) of the compound of Example 6.1 is dissolved in 15 ml of THF and 15 ml of dichloromethane and combined with 217 mg (0.99 mmol) of 4-(2-piperazin-1-ylethyl)morpholine. 350 mg (0.99 mmol) of TBTU and 128 mg (0.99 mmol) of DIPEA are added and this mixture is stirred for 24 hours at ambient temperature. The solvent is eliminated, the residue is taken up in ethyl acetate, and washed with 10% sodium hydrogen carbonate solution, saturated sodium chloride solution and water. The organic phase is dried, evaporated down, and the crude product is triturated with diethylether/diisopropylether. In this way, 341 mg of the product is obtained. Melting point: 136° C.–138° C.

EXAMPLE 7

1-{1-[2-(2-phenylimidazo[1,2-a]pyridin-3-yl)-2-oxoethyl]piperidin-4-yl}-1,3-dihydrobenzimidazol-2-one

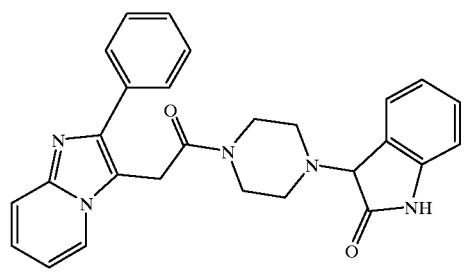

Prepared analogously to Example 6; MS: m/z 452 [(M+H)$^+$]; melting point: 263° C.–265° C.

EXAMPLE 8

1-[2-(2-phenylimidazo[1,2-a]pyridin-3-yl)-2-oxoethyl]-3-(propen-2-yl)-1,3-dihydrobenzimidazol-2-one

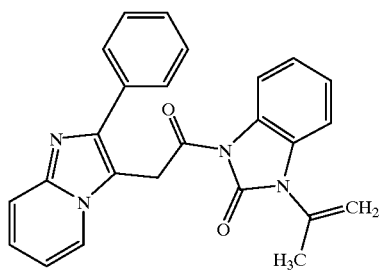

Prepared analogously to Example 6; MS: m/z 409 [(M+H)$^+$]; melting point: 167° C.

EXAMPLE 9

3-{2-[4-(2-N-Morpholinoethyl)piperazin-1-yl]ethyl}-2-phenylimidazo[1,2-a]pyridine

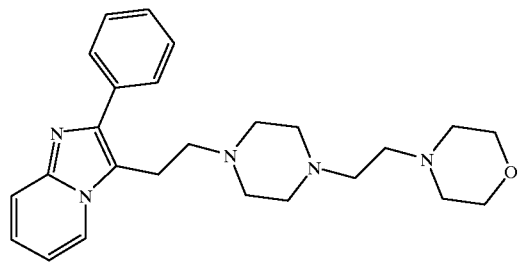

Process According to Stage O:

130 mg (0.30 mmol) of the compound of Example 6, dissolved in 10 ml of THF, is combined with 14 mg (0.30 mmol) of lithium aluminium hydride and stirred for 12 hours at ambient temperature. The solution is separated off from the precipitate, the precipitate is washed with ethyl acetate, and the combined organic solutions are evaporated down and purified by flash chromatography (dichloromethane/ethanol 90:10), to obtain 56 mg of product. MS: m/z 420 [(M+H)$^+$].

EXAMPLE 10

1-[2-(2-phenylimidazo[1,2-a]pyridin-3-yl)-2-oxoethyl]-1,3-dihydrobenzimidazol-2-one

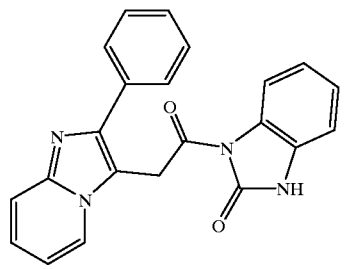

185 mg (0.50 mmol) of the compound of Example 8 is placed in 3 ml of ethanol and combined with 0.36 ml of ethanolic hydrochloric acid. The mixture is stirred for 72 hours, the solvent is eliminated and the crystalline solid is triturated with dichloromethane/ethanol 95:5 to obtain 120 mg of the product. MS: m/z 396 [(M+H)$^+$]; melting point 233° C.–235° C.

EXAMPLE 11

1-[1-(3-imidazol[1,2-a]pyridin-3-ylpropyl)piperidin-4-yl]-1,3-dihydrobenzimidazol-2-one

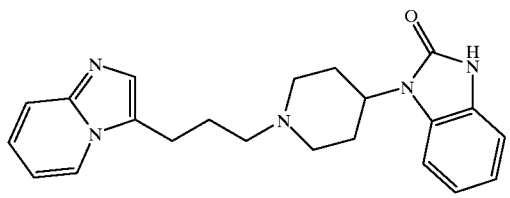

11.1.: 3-(2-ethoxycarbonyl-(E)-vinyl)imidazo[1,2-a]pyridine (Corresponds to the Compound of Formula (XV))
Process According to Stage H:

7.60 g of sodium tert-amylate is placed in 420 ml of toluene, cooled to –20° C. and 15.4 g (68.8 mmol) of triethyl phosphonoacetate dissolved in 200 ml of toluene is added dropwise within 30 minutes. The resulting mixture is stirred for 2.5 hours at ambient temperature, cooled to –5° C. and 5.00 g (34.2 mmol) of the compound of Example 1.5.1 dissolved in 210 ml of toluene is added dropwise within 30 minutes. Then the mixture is refluxed for 4 hours. The solvent is then removed, the residue is taken up in ethyl acetate, washed with water, the organic phase is dried and evaporated down. The crude product is stirred with isopropyl ether and yields 5.10 g of crystalline product. Melting point 128° C.

11.2.: 3-(3-hydroxypropyl)imidazo[1,2-a]pyridine (Corresponds to the Compound of Formula (XVII))
Process According to Stage Q:

290 mg (2.61 mmol) of calcium chloride is dissolved in 10 ml of ethanol and combined with a solution of 500 mg (2,31 mmol) of the compound of Example 11.1 in 15 ml of THF. The mixture is cooled to –15° C. and 250 mg (6.60 mmol) of sodium borohydride is added batchwise. The resulting mixture is initially stirred for 3 hours at 0° C. and then left to stand for 72 hours at 4° C. The suspension is combined with 2 N hydrochloric acid and then made alkaline with concentrated ammonia solution. The organic solvents are distilled off and the residue is combined with saturated potassium carbonate solution. This is extracted with ethyl acetate, dried and evaporated down. The crude product is purified by flash chromatography (dichloromethane/ethanol 95:5), producing 195 mg of the desired compound as a yellowish oil. MS: m/z 177 [(M+H)$^+$].

11.3.: 3-(3-bromopropyl)imidazo[1,2-a]pyridine (Corresponds to the Compound of Formula (XVIII))
Process According to Stage F:

195 mg (1.10 mmol) of the compound of Example 11.2 is dissolved in 2 ml of chloroform and 315 mg (1.50 mmol) of thionyl bromide is added in 5 batches while cooling with ice. The mixture is stirred for 4 hours at 0° C., combined with dichloromethane and concentrated by evaporation. The residue is divided between water and dichloromethane, adjusted to pH 7 with 1 N NaOH and extracted with dichloromethane. The combined organic phases are dried and evaporated down. 240 mg of a slowly crystallizing oil is obtained.

11.4.: 1-[1-(3-imidazo[1,2-a]pyridin-3-ylpropyl)piperidin-4-yl]-1,3-dihydrobenzimidazol-2-one
Process According to Stage G:

240 mg (2.21 mmol) of 1-piperidin-4-yl-1,3-dihydrobenzimidazol-2-one is dissolved in 3.5 ml of acetonitrile and 3.5 ml of DMF at 50° C. and at this temperature a solution of 240 mg (1.00 mmol) of the compound of Example 11.3 in 7.5 ml of ethyl acetate is added dropwise. The mixture is initially stirred for 5 hours at 50° C., then for 72 hours at RT. The solution is evaporated down and the residue is purified by flash chromatography (dichloromethane/ethanol 90:10), yielding 48 mg of product. MS: m/z 376 [(M+H)$^+$]; melting point: 185° C.

EXAMPLE 12

1-{1-[3-(2-phenylimidazo[1,2-a]pyridin-3-yl)propyl]piperidin-4-yl}-1,3-dihydrobenzimidazol-2-one

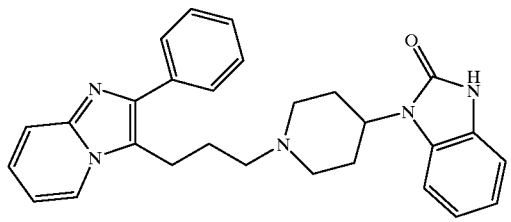

Prepared analogously to Example 11; melting point: 98° C.

EXAMPLE 13

1-{1-[3-(2-p-chlorophenylimidazo[1,2-a]pyridin-3-yl)propyl]piperidin-4-yl}-1,3-dihydrobenzimidazol-2-one

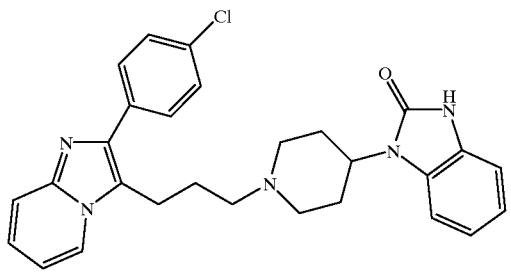

13.1.: Ethyl 5-(4-chlorophenyl)-5-oxo-4-bromopentanoate (Corresponds to the Compound According to Formula (XX))
Process According to Stage K:

5.00 g (19.6 mmol) of ethyl 5-(4-chlorophenyl)-5-oxopentanoate (corresponds to the compound according to formula (XIX)) is dissolved in 50 ml of ether and at –15° C., 4.00 g (25.0 mmol) of bromine is added dropwise. The mixture is refluxed for 2 hours. The reaction mixture is washed with water, the organic phase is dried and evaporated down. 5.90 g of the product is obtained in the form of a light brown oil.

13.2.: 3-(2-ethoxycarbonylethyl)-2-(4-chlorophenyl)imidazo[1,2-a]pyridine (Corresponds to the Compound of Formula (XXI))
Process According to Stage L:

3.29 g (35.0 mmol) of 2-aminopyridine (corresponds to the compound according to formula (XIII) is taken and combined with 5.90 g (17.7 mmol) of the compound of Example 13.1. The mixture is refluxed for 2.5 hours and the solvent is then removed. The residue is divided between ether and water, the organic phase is washed with water and extracted with 2 N hydrochloric acid. The aqueous phase is made alkaline with concentrated ammonia solution and extracted with ether. The combined organic phases are dried, evaporated down and the residue is triturated with diisopropyl ether. In this way, 1.60 g of the product is obtained as a crystalline solid.

13.3.: 3-(3-hydroxypropyl)-2-(4-chlorophenyl)imidazo[1,2-a]pyridine (Corresponds to the Compound of Formula (XVII))

Process According to Stage E:

1.00 g (9.01 mmol) of calcium chloride is dissolved in 10 ml of ethanol and a solution of 1.60 g (4.87 mmol) of the product from stage B in 16 ml of THF is added. The resulting mixture is cooled to −10° C. and 450 mg (11.9 mmol) of sodium borohydride is added batchwise. It is then allowed to come up to 0° C., stirred for 6 hours at this temperature and then left to stand for 72 5 hours at 4° C. It is combined with 2 N hydrochloric acid solution and made alkaline with concentrated ammonia solution. The organic solvents are distilled off and the aqueous phase is adjusted to pH 12 with potassium carbonate. Extraction with ethyl acetate, drying of the combined organic phases and evaporation yields 750 mg of product.

13.4.: 1-{1-[3-(2-p-chlorophenylimidazo[1,2-a]pyridin-3-yl)propyl]piperidin-4-yl}-1,3-dihydrobenzimidazol-2-one Starting from the compound of Example 13.3. the title compound is synthesized analogously to the procedure according to Example 11.3 (process according to stage F) and then according to Example 11.4 (process according to stage G). Melting point: 236° C.

EXAMPLE 14

3-[3-(4-benzylpiperazin-1-yl)propyl]-2-(4-chlorophenyl)imidazo[1,2-a]pyridine

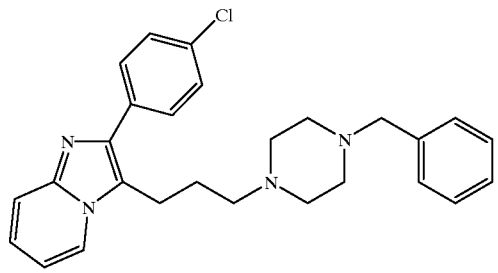

Prepared analogously to Example 13; melting point 174° C.

EXAMPLE 15

3-[3-(4-phenylpiperazin-1-yl)propyl]-2-(4-chlorophenyl)imidazo[1,2-a]pyridine

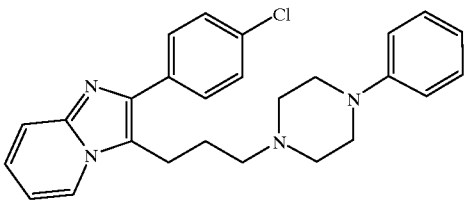

Prepared analogously to Example 13; melting point 169° C.

EXAMPLE 16

3-{3-[4-(4-Trifluorophenyl)piperazin-1-yl]propyl}-2-(4-chlorophenyl)imidazo[1,2-a]pyridine

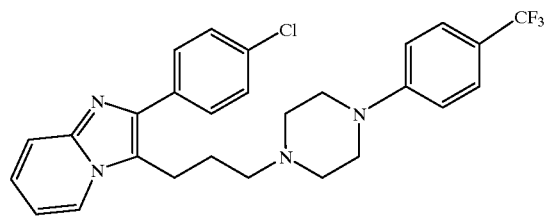

Prepared analogously to Example 13; melting point 174° C.

EXAMPLE 17

3-{3-[4-(4-methylphenyl)piperazin-1-yl]propyl}-2-(4-chlorophenyl)imidazo[1,2-a]pyridine

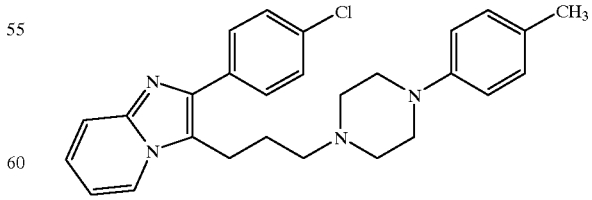

Prepared analogously to Example 13; melting point 154° C.

EXAMPLE 18

3-{3-[4-(2-phenylethyl)piperazin-1-yl]propyl}-2-(4-chlorophenyl)imidazo[1,2-a]pyridine

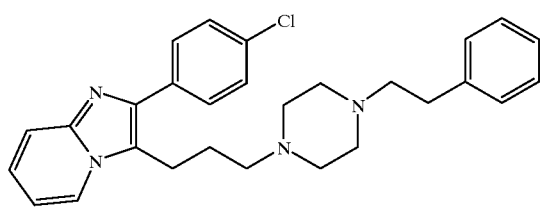

Prepared analogously to Example 13; melting point 156° C.

EXAMPLE 19

3-{3-[4-(4-chlorobenzyl)piperazin-1-yl]-3-oxopropyl}-2-(4-chlorophenyl)imidazo[1,2-a]pyridine

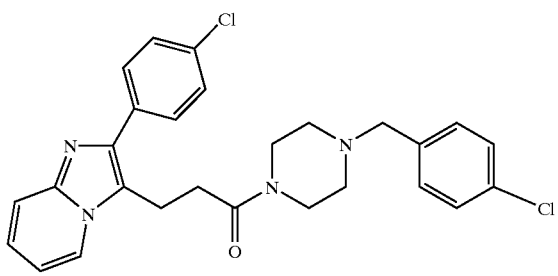

19.1.: 3-Carboxypropyl-2-(4-chlorophenyl)imidazo[1,2-a]pyridine (Corresponds to the Compound of Formula (XXII))

Process According to Stage M:

3.50 g (10.7 mmol) of the compound of Example 13.2 in 35 ml of ethanol is refluxed together with 12 ml of 40% sodium hydroxide solution for 2 hours and then the solvent is eliminated. The residue is dissolved in 400 ml of water. It is adjusted to pH 1 with concentrated hydrochloric acid, the crystals precipitated are separated off and dried in vacuo to obtain 3.03 g of product.

19.2.: 3-{3-[4-(4-chlorobenzyl)piperazin-1-yl]-3-oxopropyl}-2-(4-chlorophenyl)imidazo[1,2-a]pyridine Process According to Stage N:

300 mg (1.00 mmol) of the compound of Example 19.1 is dissolved in 7.5 ml of THF and 7.5 ml of dichloromethane and combined with 211 mg (1.00 mmol) of 1-(4-chlorobenzyl)piperazine. 353 mg (1.10 mmol) of TBTU and 129 mg (1.00 mmol) of DIPEA are added and the mixture is stirred for 16 hours at ambient temperature. The solvent is eliminated, the residue is taken up in ethyl acetate and washed with 10% sodium hydrogen carbonate solution, saturated sodium chloride solution and water. The organic phase is dried, evaporated down and the crude product is triturated with diisopropylether. In this way, 190 mg of the product is obtained. Melting point: 159° C.

EXAMPLE 20

3-{3-[4-(4-chlorobenzyl)piperazin-1-yl]propyl}-2-(4-chlorophenyl)imidazo[1,2-a]pyridine

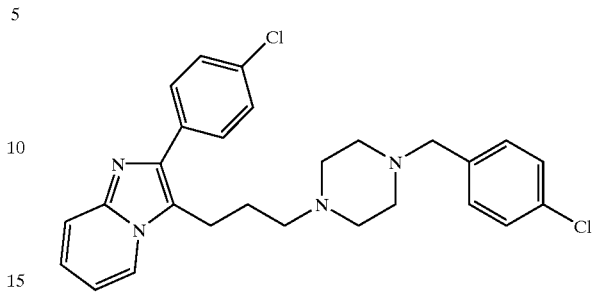

Process According to Stage O:

160 mg (0.32 mmol) of the compound of Example 19 is dissolved in 10 ml of THF and 4 ml (4 mmol) of a 1 M solution of borane/tetrahydrofuran complex in THF is added while cooling with ice. The mixture is stirred for 3 hours while cooling with ice and combined with 8 ml of 1 N hydrochloric acid. Then it is adjusted to pH 8 with 10% sodium hydrogen carbonate solution. It is concentrated by evaporation, and the residue is extracted with ethyl acetate. Drying and purifying by flash chromatography (dichloromethane/ethanol 95:5) yields 10 mg of the product.

EXAMPLE 21

1-[3-(2-phenylimidazo[1,2-a]pyridin-3-yl)-1-oxo-2(E)propenyl]piperidin-4-yl}-1,3-dihydrobenzimidazol-2-one

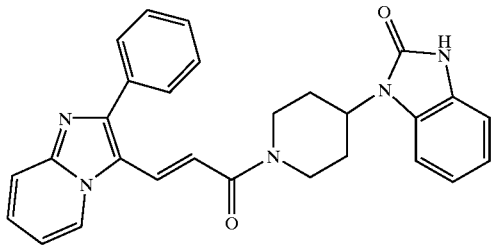

21.1.: 3-(2-Carboxy-(E)-vinyl)-2-phenylimidazo[1,2-a]pyridine (Corresponds to the Compound of Formula (XVI))

Process According to Stage M:

0.90 g 3-(2-ethoxycarbonyl-(E)-vinyl)-2-phenylimidazo[1,2-a]pyridine (obtainable according to the process in stage H analogously to Example 11.1) in 10 ml of ethanol is combined with 3 ml of 40% sodium hydroxide solution and refluxed for 2 hours. The mixture is cooled and the crystals precipitated are separated off. These are dissolved in 10 ml of water and concentrated hydrochloric acid is added dropwise while cooling with ice. The crystals precipitated are washed with water and dried to obtain 438 mg of product.

21.2.: 1-[3-(2-phenylimidazo[1,2-a]pyridin-3-yl)-1-oxo-2(E)propenyl]piperidin-4-yl}-1,3-dihydrobenzimidazol-2-one Process According to Stage N:

200 mg (0.81 mmol) of the compound of Example 21.2 is dissolved in 10 ml of THF and 10 ml of dichloromethane and combined with 175 mg (0.81 mmol) of 1-piperidin-4-yl-1,3-dihydrobenzimidazol-2-one. 289 mg (0.90 mmol) of TBTU and 116 mg (0.90 mmol) of DIPEA are added and the mixture is stirred for 20 hours at ambient temperature. The solvent is eliminated, the residue is taken up in ethyl acetate and washed with 10% sodium hydrogen carbonate solution, saturated sodium chloride solution and water. The organic phase is dried, evaporated down and the crude product is triturated with diethylether. In this way, 136 mg of the product is obtained. Melting point: >230° C.

EXAMPLE 22

3-{3-[4-(4-chlorobenzyl)piperazin-1-yl]-1-oxo-2(E)-propenyl}-2-phenyl-6-chloroimidazo[1,2-a]pyridine

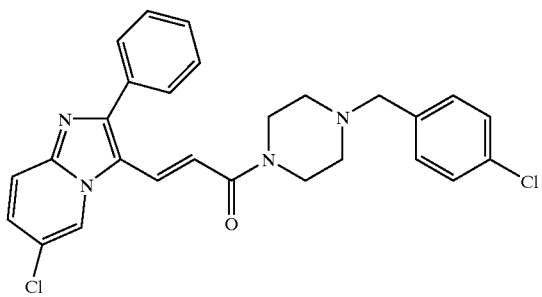

Prepared analogously to Example 21; melting point: 104° C.

EXAMPLE 23

1-[3-(imidazo[1,2-a]pyridin-3-yl)-1-oxo-2(E)propenyl]piperidin-4-yl}-1,3-dihydrobenzimidazol-2-one

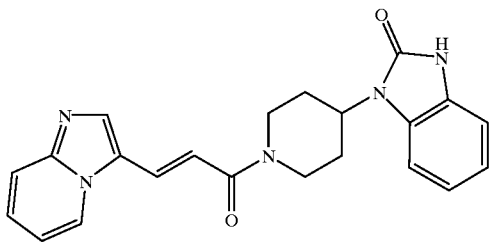

Prepared analogously to Example 21; melting point: 230° C. (decomp.).

EXAMPLE 24

1-[3-(6-chloro-2-methylimidazo[1,2-a]pyridin-3-yl)-1-oxo-2(E)propenyl]-piperidin-4-yl}-1,3-dihydrobenzimidazol-2-one

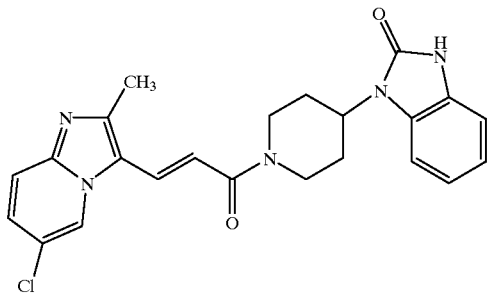

Prepared analogously to Example 21; melting point: 178° C.–180° C.

EXAMPLE 25

1-{3-[2-(4-methoxyphenyl)imidazo[1,2-a]pyridin-3-yl]-1-oxo-2(E)propenyl}piperidin-4-yl}-1,3-dihydrobenzimidazol-2-one

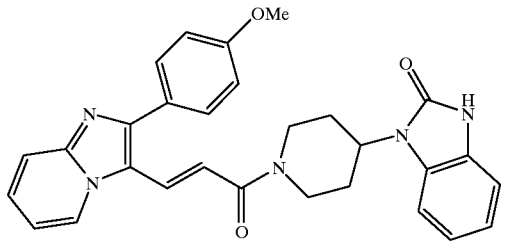

Prepared analogously to Example 21; melting point: 219° C.

EXAMPLE 26

1-[3-(2-Trifluoromethylimidazo[1,2-a]pyridin-3-yl)-1-oxo-2(E)propenyl]piperidin-4-yl}-1,3-dihydrobenzimidazol-2-one

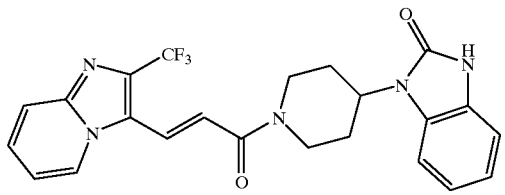

Prepared analogously to Example 21; melting point: 198° C.

EXAMPLE 27

3-{3-[4-(4-benzyl)piperidin-1-yl]-1-oxo-2(E)-propenyl}-2-phenyl-6-chloroimidazol[1,2-a]pyridine

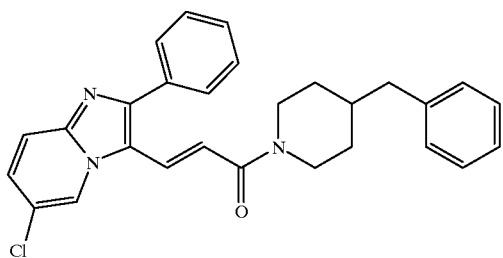

Prepared analogously to Example 21; melting point: 179° C.–183° C.

EXAMPLE 28

3-{3-[4-(4-phenyl)piperidin-1-yl]-1-oxo-2(E)-propenyl}-2-phenyl-6-chloroimidazol[1,2-a]pyridine

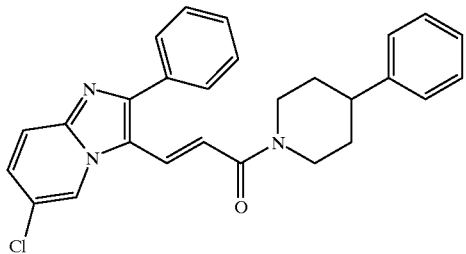

Prepared analogously to Example 21; melting point: 170° C.–172° C.

The compounds according to the invention are characterized in that they inhibit the process of the formation of Aβ or its release from cells. This property was investigated according to the test described below.

The inhibition of Aβ formation was investigated in the medium of a cell line overexpressing APP751. For this purpose, human astroglioma cells (U 373, ATCC) were stably transfected with the gene for human APP751 under the control of a CMV promoter (vector pRC-CMV). A clone with a high APP751 expression (U373-K10) was selected. In order to carry out the assay the cells are plated out in 96-well plates (Falcon) in Dulbecco's-Minimal-Essential medium (DMEM, Bio-Whittaker) with 10% FCS and cultivated to confluence at 37° C./5% $CO_2$.

The substances to be tested are first dissolved in 100% DMSO and then diluted to the test concentration in culture medium, so that the DMSO concentration of the test solution is always below 0.5%.

150 µl of the test solution are added per well to a confluent culture plate which has previously been washed once with DMEM, and pre-incubated for about 16 hours. This solution is replaced by 150 µl of fresh test solution after 1 wash and incubated again for 4 hours.

100 µl of this four-hour supernatant are transferred to an ELISA plate (Nunc) coated with the antibody 6E10 (specific for Aβ1-16, Senetek), and incubated overnight at 4° C. The Aβ is determined the next day by means of the alkaline phosphatase-conjugated antibody 6B10, which is specific for Aβ32-40.

The $IC_{50}$ values obtained for the compounds according to the invention are shown in Table 1.

TABLE 1

| Example | $IC_{50}$ value [µM] |
|---|---|
| 1 | 12 |
| 2 | 5 |
| 11 | 6 |
| 12 | 12 |
| 13 | 15 |
| 14 | 30 |
| 20 | 35 |
| 21 | 20 |

The compounds according to the invention may be administered orally, transdermally, intrathecally, by inhalation or parenterally and occur as active ingredients in conventional preparations, for example in compositions which consist essentially of an inert pharmaceutical carrier and an effective dose of the active substance, such as for example tablets, coated tablets, capsules, lozenges, powders, solutions, suspensions, emulsions, syrups, suppositories, transdermal systems, etc. An effective dose of the compounds according to the invention is between 1 mg/dose and 5000 mg/dose, preferably between 10 mg/dose and 1000 mg/dose, most preferably between 10 mg/dose to 100 mg/dose for oral administration, and between 0.001 mg/dose and 100 mg/dose, preferably between 0.1 mg/dose and 10 mg/dose for intravenous or intramuscular administration. For inhalation, according to the invention, solutions containing 0.01% to 1.0%, preferably 0.1% to 0.5% active substance are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions, or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g., with the addition of preservatives such as p-hydroxybenzoates, or stabilizers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 mg and 5000 mg, preferably 100 mg to 1000 mg per adult.

The Examples which follow illustrate the present invention without restricting its scope:

EXAMPLES OF PHARMACEUTICAL FORMULATIONS

A. TABLETS

| Component | Amount per tablet (mg) |
| --- | --- |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
| --- | --- |
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
| --- | --- |
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
| --- | --- |
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
| --- | --- |
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

| F. SUPPOSITORIES | |
|---|---|
| Component | Amount per suppository (mg) |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

We claim:

1. A compound of general formula (I)

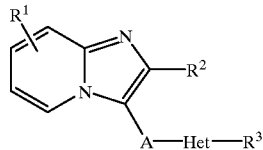

(I)

wherein:

A is —CH₂—CH₂—, —CH₂—CH₂—CH₂—, or —CH=CH—CO—;

Het is piperidinyl; and

R³ is 2-hydroxyethyl, phenyl, benzyl, 4-chlorobenzyl, or 1,3-dihydrobenzimidazol-2-on-1-yl, or an optical isomer, enantiomer, tautomer, free base, or pharmacologically acceptable acid addition salt thereof.

2. The compound of general formula (I) according to claim 1, wherein:

R¹ is hydrogen;

R² is hydrogen, methyl, phenyl, or 4-chlorophenyl; and

R³ is benzyl, 4-chlorobenzyl, or 1,3-dihydrobenzimidazol-2-on-1-yl, or an optical isomer, enantiomer, tautomer, free base, or pharmacologically acceptable acid addition salt thereof.

3. A compound of general formula (I)

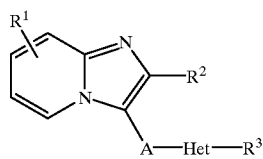

(I)

wherein:

A is —CH₂—, —CH₂—CH₂—, —CH₂—CH₂—CH₂—, —CH₂—CH₂—CH₂—CH₂—, —CH₂—CH₂—CO—, or —CH=CH—CO—;

R¹ is hydrogen or halogen;

R² is hydrogen, C₁–C₄-alkyl, CF₃, or a phenyl group optionally substituted by halogen, C₁–C₄-alkyl, or C₁–C₄-alkyloxy; and -Het-R³ is

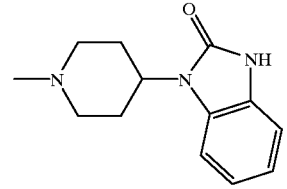

or an optical isomer, enantiomer, tautomer, free base, or pharmacologically acceptable acid addition salt thereof.

4. A pharmaceutical composition comprising an effective amount of a compound of general formula (I) according to claim 1 and an inert pharmaceutical carrier.

5. A pharmaceutical composition comprising an effective amount of a compound of general formula (I) according to claim 2 and an inert pharmaceutical carrier.

6. A pharmaceutical composition comprising an effective amount of a compound of general formula (I) according to claim 3 and an inert pharmaceutical carrier.

7. A method for treatment of diseases in which a therapeutic benefit can be obtained by interfering in the process of the formation of Aβ or its release from cells, by inhibiting the Aβ activity, in a host in need of such treatment, which method comprises administering the host an effective amount of a compound of general formula (I)

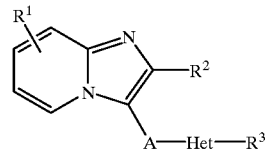

(I)

wherein:

A is —CH₂—, —CH₂—CH₂—, —CH₂—CH₂—CH₂—, —CH₂—CH₂—CH₂—CH₂—, —CH₂—CH₂—CO—, or —CH=CH—CO—;

Het is piperidinyl;

R¹ is hydrogen or halogen;

R² is hydrogen, C₁–C₄-alkyl, CF₃, or a phenyl group optionally substituted by halogen, C₁–C₄-alkyl, or C₁–C₄-alkyloxy; and R³ is hydrogen, C₁–C₄-alkyl, HO—C₁–C₄-alkyl, or C₂–C₄-alkenyl; or a group selected from phenyl, benzyl, and phenylethyl, each optionally substituted by halogen, CF₃, C₁–C₄-alkyl, or C₁–C₄-alkyloxy; or a heterocycle selected from among morpholine, piperidine, piperazine, and dihydrobenzimidazolone, the heterocycle either linked directly or via a C₁–C₄-alkylene bridge, or an optical isomer, enantiomer, tautomer, free base, or pharmacologically acceptable acid addition salt thereof.

8. A method for treatment of diseases in which a therapeutic benefit can be obtained by interfering in the process of the formation of Aβ or its release from cells, by inhibiting the Aβ activity, in a host in need of such treatment, which method comprises administering the host an effective amount of a compound of general formula (I)

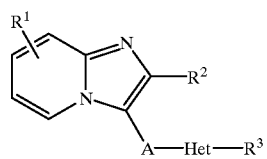

wherein:

A is —CH$_2$—CH$_2$—, —CH$_2$—CH$_2$—CH$_2$—, or —CH=CH—CO—;

Het is piperidinyl;

R$^1$ is hydrogen or halogen;

R$^2$ is hydrogen, C$_1$–C$_4$-alkyl, CF$_3$, phenyl, halogen-substituted phenyl, or C$_1$–C$_4$-alkyloxy-substituted phenyl; and R$^3$ is C$_1$–C$_4$-alkyl, HO—C$_1$–C$_4$-alkyl, C$_2$–C$_4$-alkenyl, phenyl, benzyl, phenylethyl, halogen-substituted phenyl, or halogen-substituted benzyl; or a heterocycle selected from among morpholine and dihydrobenzimidazolone, the heterocycle either linked directly or via a C$_1$–C$_4$-alkylene bridge, or an optical isomer, enantiomer, tautomer, free base, or pharmacologically acceptable acid addition salt thereof.

9. A method for treatment of diseases in which a therapeutic benefit can be obtained by interfering in the process of the formation of Aβ or its release from cells, by inhibiting the Aβ activity, in a host in need of such treatment, which method comprises administering the host an effective amount of a compound of general formula (I)

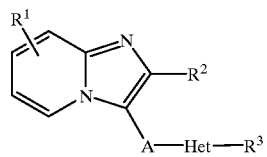

wherein:

A is —CH$_2$—CH$_2$—, —CH$_2$—CH$_2$—CH$_2$—, or —CH=CH—CO—;

Het is piperidinyl;

R$^1$ is hydrogen or chlorine;

R$^2$ is hydrogen, methyl, phenyl, or 4-chlorophenyl; and

R$^3$ is C$_1$–C$_4$-alkyl, HO—C$_1$–C$_4$-alkyl, C$_2$–C$_4$-alkenyl, phenyl, benzyl, or halogen-substituted benzyl; or a heterocycle selected from morpholine and dihydrobenzimidazolone, the heterocycle either linked directly or via a C$_1$–C$_4$-alkylene bridge, or an optical isomer, enantiomer, tautomer, free base, or pharmacologically acceptable acid addition salt thereof.

10. A method for treatment of diseases in which a therapeutic benefit can be obtained by interfering in the process of the formation of Aβ or its release from cells, by inhibiting the Aβ activity, in a host in need of such treatment, which method comprises administering the host an effective amount of a compound of general formula (I) according to claim 1.

11. A method for treatment of diseases in which a therapeutic benefit can be obtained by interfering in the process of the formation of Aβ or its release from cells, by inhibiting the Aβ activity, in a host in need of such treatment, which method comprises administering the host an effective amount of a compound of general formula (I) according to claim 2.

12. A method for treatment of diseases in which a therapeutic benefit can be obtained by interfering in the process of the formation of Aβ or its release from cells, by inhibiting the Aβ activity, in a host in need of such treatment, which method comprises administering the host an effective amount of a compound of general formula (I) according to claim 3.

13. The method according to claim 7, wherein the disease is Alzheimer's disease.

14. A process for preparing compounds of general formula (I)

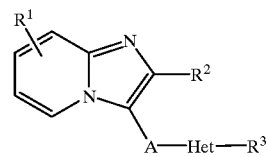

wherein:

A is —CH$_2$—CH$_2$— or —CH$_2$—CH$_2$—CH$_2$—;

Het is piperidinyl;

R$^1$ is hydrogen or halogen;

R$^2$ is hydrogen, C$_1$–C$_4$-alkyl, CF$_3$, or a phenyl group optionally substituted by halogen, C$_1$–C$_4$-alkyl, or C$_1$–C$_4$-alkyloxy; and R$^3$ is hydrogen, C$_1$–C$_4$-alkyl, HO—C$_1$–C$_4$-alkyl, or C$_2$–C$_4$-alkenyl; or a group selected from phenyl, benzyl, and phenylethyl, each optionally substituted by halogen, CF$_3$, C$_1$–C$_4$-alkyl, or C$_1$–C$_4$-alkyloxy; or a heterocycle selected from among morpholine, piperidine, piperazine, and dihydrobenzimidazolone, the heterocycle either linked directly or via a C$_1$–C$_4$-alkylene bridge, or an optical isomer, enantiomer, tautomer, free base, or pharmacologically acceptable acid addition salt thereof, the method comprising: reacting a compound of formula (VIII)

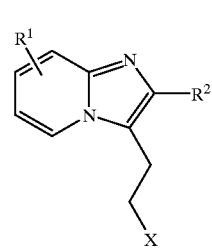

or a compound of formula (XIII)

(XVIII)

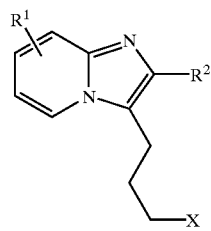

wherein X is chlorine, bromine, or iodine, with an amine of formula H-Het-R³.

15. A process for preparing compounds of general formula (I)

(I)

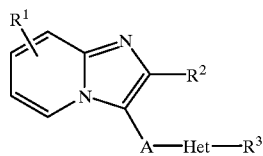

wherein:

A is —CH₂—CH₂—CO—, or —CH=CH—CO—;
Het is piperidinyl;
R¹ is hydrogen or halogen;
R² is hydrogen, C₁–C₄-alkyl, CF₃, or a phenyl group optionally substituted by halogen, C₁–C₄-alkyl, or C₁–C₄-alkyloxy; and
R³ is hydrogen, C₁–C₄-alkyl, HO—C₁–C₄-alkyl, or C₂–C₄-alkenyl; or a group selected from phenyl, benzyl, and phenylethyl, each optionally substituted by halogen, CF₃, C₁–C₄-alkyl, or C₁–C₄-alkyloxy; or a heterocycle selected from among morpholine, piperidine, piperazine, and dihydrobenzimidazolone, the heterocycle either linked directly or via a C₁–C₄-alkylene bridge, or an optical isomer, enantiomer, tautomer, free base, or pharmacologically acceptable acid addition salt thereof, the method comprising: reacting a carboxylic acid of formula (XIV), (XXII), or (XVI)

(XIV)

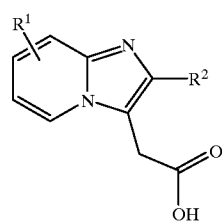

(XXII)

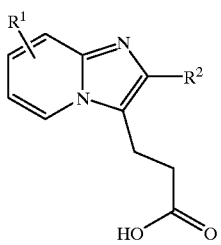

(XVI)

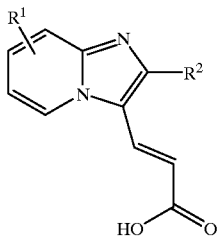

with an amine of formula H-Het-R³, optionally using coupling reagents.

16. A process for preparing compounds of general formula (I)

(I)

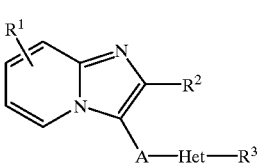

wherein:

A is —CH₂—CH₂— or —CH₂—CH₂—CH₂—;
Het is piperidinyl;
R¹ is hydrogen or halogen;
R² is hydrogen, C₁–C₄-alkyl, CF₃, or a phenyl group optionally substituted by halogen, C₁–C₄-alkyl, or C₁–C₄-alkyloxy; and
R³ is hydrogen, C₁–C₄-alkyl, HO—C₁–C₄-alkyl, or C₂–C₄-alkenyl; or a group selected from phenyl, benzyl, and phenylethyl, each optionally substituted by halogen, CF₃, C₁–C₄-alkyl, or C₁–C₄-alkyloxy; or a heterocycle selected from among morpholine, piperidine, piperazine, and dihydrobenzimidazolone, the heterocycle either linked directly or via a C₁–C₄-alkylene bridge, or an optical isomer, enantiomer, tautomer, free base, or pharmacologically acceptable acid addition salt thereof, the method comprising reducing compounds of formula (I) wherein A is —CH₂CO— or —CH₂—CH₂—CO—.

* * * * *